(12) United States Patent
Rohit et al.

(10) Patent No.: US 11,847,817 B2
(45) Date of Patent: Dec. 19, 2023

(54) METHODS AND SYSTEMS FOR AUTOMATED ASSESSMENT OF SPERMATOGENESIS

(71) Applicant: AIRAMATRIX PRIVATE LIMITED, Maharashtra (IN)

(72) Inventors: Rohit, Haryana (IN); Pranab Samanta, West Bengal (IN)

(73) Assignee: AIRAMATRIX PRIVATE LIMITED, Maharashtra (IN)

( * ) Notice: Subject to any disclaimer, the term of this patent is extended or adjusted under 35 U.S.C. 154(b) by 718 days.

(21) Appl. No.: 17/022,089

(22) Filed: Sep. 16, 2020

(65) Prior Publication Data

US 2021/0080450 A1    Mar. 18, 2021

(30) Foreign Application Priority Data

Sep. 16, 2019   (IN) .............................. 201921037223

(51) Int. Cl.
| | |
|---|---|
| G06V 10/764 | (2022.01) |
| G16H 10/40 | (2018.01) |
| G16H 30/20 | (2018.01) |
| G16H 50/20 | (2018.01) |
| G16H 30/40 | (2018.01) |
| G01N 1/28 | (2006.01) |
| G01N 1/30 | (2006.01) |
| G01N 1/36 | (2006.01) |
| G01N 33/483 | (2006.01) |

(Continued)

(52) U.S. Cl.
CPC ........... *G06V 10/764* (2022.01); *G01N 1/286* (2013.01); *G01N 1/30* (2013.01); *G01N 1/36* (2013.01); *G01N 33/4833* (2013.01); *G06V 10/82* (2022.01); *G06V 20/695* (2022.01); *G06V 20/698* (2022.01); *G16H 10/40* (2018.01); *G16H 30/20* (2018.01); *G16H 30/40* (2018.01); *G16H 50/20* (2018.01); *G01N 2001/2873* (2013.01)

(58) Field of Classification Search
CPC ........ G16H 10/40; G16H 30/20; G16H 50/20; G16H 30/40; G06V 10/82; G01N 33/4833

See application file for complete search history.

(56) References Cited

U.S. PATENT DOCUMENTS

| | | | | |
|---|---|---|---|---|
| 2009/0246771 | A1* | 10/2009 | Laird ................... | C12Q 1/6883 435/6.14 |
| 2011/0236903 | A1* | 9/2011 | McClelland ......... | C12Q 1/6886 435/6.1 |

* cited by examiner

*Primary Examiner* — Edward Park

(57) ABSTRACT

Methods and systems for automated assessment of spermatogenesis. Embodiments disclosed herein relate to drug development and testicular toxicity in safety evaluation studies, and more particularly to automatic assessment of spermatogenesis through a staging of seminiferous tubules using Artificial Intelligence/deep learning methods. A method disclosed herein includes detecting the seminiferous tubules by analyzing a testes tissue specimen and mapping the seminiferous tubules to detect and segment germ cells. The method includes classifying the seminiferous tubules into respective stages based on the segmented germ cells. The method further includes categorizing the seminiferous tubules into a normal category and an abnormal category based on the segmented germ cells. The method further includes categorizing the testes tissue specimen into the normal category and the abnormal category based on the classification of the seminiferous tubules for toxicity analysis.

14 Claims, 20 Drawing Sheets
(9 of 20 Drawing Sheet(s) Filed in Color)

(51) Int. Cl.
*G06V 20/69* (2022.01)
*G06V 10/82* (2022.01)

ROUND SPERMATIDS SEGMENTATION

BASOPHILIC GRANULES/RESIDUAL BODIES WITH LUMEN AREA SEGMENTATION

PACHYTENE SEGMENTATION

ELONGATED SPERMATIDS SEGMENTATION

| Stages | Characteristic Features |
|---|---|
| 1 | ESp heads: limited bundling; ESp location: close to lumen with very few moving towards base; Spc size: smaller than stages 2/3 |
| 2, 3 | ESp heads: frequent bundling; ESp location: majority in the mid-epithelial region; Spc size: smaller than stages 4/5 and 6 |
| 4, 5 | ESp heads: prominent bundling; ESp location: majority within lower third of the epithelium; Spc size: larger than stages 2/3 |
| 6 | ESp heads: prominent bundling; ESp location: majority towards lumen; Spc size: larger than stages 4/5 |
| 7 | RSp shape: round; ESp location: aligned around the lumen; RB size: smaller than stage 8; RB location: random with respect to ESp heads |
| 8 | RSp shape: slightly eccentric; RB size: larger than stage 7; RB position: mostly below ESp heads |
| 9 | RSp shape: towards elliptical; RB location: may be present in lumen and within epithelium; No ESp |
| 10 | RSp shape: elliptical and starts to elongate; RB location: may be present in lower third and base of epithelium; No ESp |
| 11 | ESp shape: banana shape; RB location: may lie in the lower third and base of epithelium; No RSp |
| 12 | ESp shape: longer and thinner than stage 11; Chromatin density of large pachytene: denser than stage 13; No RSp |
| 13 | ESp shape: similar or thinner than stage 12; Chromatin density of large pachytene: less than stage 12; No RSp |
| 14 | ESp shape: similar to stage 13; At least one MB; RSp may also be present |

FIG. 6B

| STAIN | AVERAGE ACCURACY | AVERAGE PRECISION |
|-------|------------------|-------------------|
| H&E   | 82.88%           | 82.94%            |
| PAS   | 80.91%           | 83.66%            |

FIG. 10

METHODS AND SYSTEMS FOR AUTOMATED ASSESSMENT OF SPERMATOGENESIS

CROSS REFERENCE TO RELATED APPLICATION

This application is based on and derives the benefit of Indian Provisional Application 201921037223 filed on 16 Sep. 2019, the contents of which are incorporated herein by reference.

TECHNICAL FIELD

Embodiments disclosed herein relate to assessing spermatogenesis, and more particularly to automatic assessment of spermatogenesis through a staging of seminiferous tubules.

BACKGROUND

In general, toxicology studies of male reproductive functions have received increased interest due to growing reports of falling sperm counts and rising reproductive disorders, infertility, or the like. The toxological effects on the male reproductive function may be detected by identifying disturbances in spermatogenesis, wherein spermatogenesis involves production of the sperm from primordial germ cells.

Testicular tissue may be examined with an awareness of a spermatogenic cycle to ensure the identification of the subtle disturbances in the spermatogenesis. A histopathological examination of testicular/testes tissue can be performed for detecting the toxological effects on the male reproductive function. The histopathological examination can serve as a sensitive and early indicator of the subtle disturbances in the spermatogenesis.

A conventional histopathological examination may involve detecting seminiferous tubules (that can be made up of columnar Sertoli cells and surrounded by spermatogenic cells) from the testicular tissue, and classifying the detected seminiferous tubules into different stages of the spermatogenic cycle, which can be used to identify the subtle disturbances in the spermatogenesis. However, detection and classification of the seminiferous tubules into the different stages of the spermatogenic cycle may involve manual assessment, which may be a complicated and demanding task. Also, the complexity of testicular histology, close association of various germ cells, and overlapping features among adjacent stages makes manual assessment challenging and time consuming. Further, manual assessment is dependent on an expertise of a pathologist, which can be highly subjective.

In addition, in the conventional histopathological examination, for better visualization and assessment of histological features during the staging of the spermatogenic cycle, additional stained slides such as PAS (Periodic Acid Schiff) stained slides are required in addition to normal H&E (Hematoxylin and Eosin) stained slides.

OBJECTS

The principal object of embodiments herein is to disclose methods and systems for automatic assessment of spermatogenesis through a staging of seminiferous tubules.

Another object of embodiments herein is to disclose methods and systems for using Artificial Intelligence (AI)/deep learning methods for automatically assessing spermatogenesis.

Another object of embodiments herein is to disclose methods and systems for using testes tissue specimen stained with Hematoxylin and Eosin (H&E) for automatically assessing spermatogenesis.

Another object of embodiments herein is to disclose methods and systems for detecting the seminiferous tubules from the testes tissue specimen stained with H&E and classifying the seminiferous tubules into respective stages of a spermatogenic cycle based on a segmentation of germ cells.

Another object of embodiments herein is to disclose methods and systems for categorizing the seminiferous tubules into at least one of a normal category and an abnormal category based on the stages and morphological features.

Another object of embodiments herein is to disclose methods and systems for categorizing the testes tissues specimen into the normal category and the abnormal category based on the categorization of the seminiferous tubules for toxicity analysis.

These and other aspects of the embodiments herein will be better appreciated and understood when considered in conjunction with the following description and the accompanying drawings. It should be understood, however, that the following descriptions, while indicating at least one embodiment and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF FIGURES

The patent or application file contains at least one drawing and/or photograph executed in color. Copies of this patent or patent application publication with color drawing(s) and/or photograph(s) will be provided by the Office upon request and payment of the necessary fee.

Embodiments herein are illustrated in the accompanying drawings, through out which like reference letters indicate corresponding parts in the various figures. The embodiments herein will be better understood from the following description with reference to the drawings, in which:

FIGS. 6A, 6B, 6C, 6D, 6E, and 6F are example diagrams depicting automated spermatogenic staging, according to embodiments as disclosed herein;

FIG. 10 is an example table depicting average accuracy and average precision resulted from the automated spermatogenic staging, according to embodiments as disclosed herein.

DETAILED DESCRIPTION

Figure 1A:
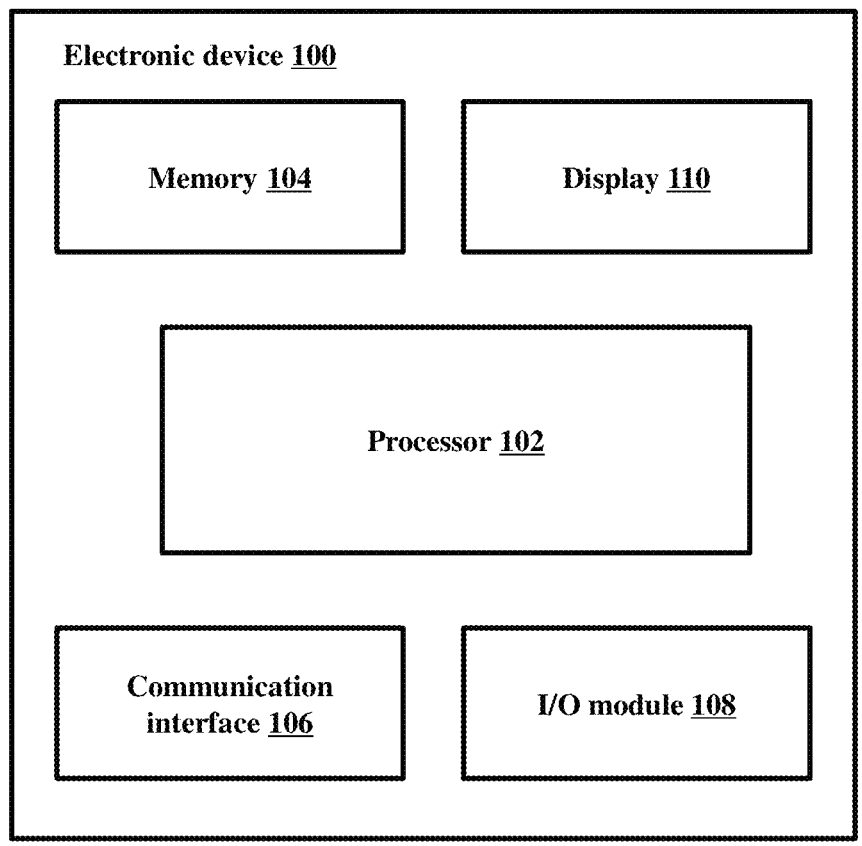
FIG. 1A depicts an electronic device, wherein the electronic device can automatically assess spermatogenesis, according to embodiments as disclosed herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Embodiments herein disclose methods and systems for automatic assessment of spermatogenesis through a staging of seminiferous tubules. Embodiments herein disclose methods and systems for using Artificial Intelligence (AI)/deep learning methods for assessment of the spermatogenesis. Embodiments herein disclose methods and systems for toxicity analysis based on the assessment of the spermatogenesis. Referring now to the drawings, and more particularly to FIGS. 1A through 10, where similar reference characters denote corresponding features consistently throughout the figures, there are shown embodiments.

FIG. 1A depicts an electronic device 100, wherein the electronic device can automatically assess spermatogenesis, according to embodiments as disclosed herein. Examples of the electronic device 100 can be, but not limited to, a mobile phone, a smart phone, a tablet, a handheld device, a phablet, a laptop, a computer, a wearable computing device, a medical equipment, an Internet of Thing (IoT) device and so on. The electronic device 100 can also be a special-purpose computing system such as, but not limited to, a server, a cloud, a multiprocessor system, a microprocessor based programmable consumer electronics, a network computer, a minicomputer, a mainframe computer, and so on. The electronic device 100 can also be a server coupled with databases (not shown). The server may be a standalone server, or a server on a cloud. The electronic device 100 can also be a cloud computing platform, that can be connected to user devices (devices used by a physician/pathologist, a user/patient, and so on) located in different geographical locations to provide information about the assessment of the spermatogenesis. The electronic device 100 referred herein can be configured to perform automated assessment of spermatogenesis, from which toxological effects on male reproductive function can be detected. The spermatogenesis can be a process of sperm cell development.

The electronic device 100 includes a processor 102, a memory 104, a communication interface 106, an Input/Output (I/O) module 108, and a display 110. In an embodiment, the electronic device 100 includes at least one imaging sensor, at least one camera, at least one scanner, and so on (not shown). In an embodiment, the electronic device 100 may be connected to at least one of the at least one imaging sensor, the at least one camera, the at least one scanner, and so on externally using a communication network (not shown). Examples of the communication network can be, but is not limited to, the Internet, a wired network (a Local Area Network (LAN), Ethernet and so on), a wireless network (a Wi-Fi network, a cellular network, a Wi-Fi Hotspot, Bluetooth, Zigbee and so on) and so on. The electronic device 100 may also be connected to at least one external entity such as, but not limited to, a server, external databases, and so on using the communication network for accessing information required for performing assessment of the spermatogenesis.

The processor 102 can be at least one of a single processer, a plurality of processors, multiple homogeneous or heterogeneous cores, multiple Central Processing Units (CPUs) of different kinds, microcontrollers, special media, and other accelerators. Further, the plurality of processing units 102 may be located on a single chip or over multiple chips.

The processor 102 can be configured to perform automated assessment of the spermatogenesis. In an embodiment, the processor 102 can perform the assessment of the spermatogenesis by classifying seminiferous tubules into stages of a spermatogenic cycle/spermatogenesis process.

For the assessment of the spermatogenesis, a testes tissue specimen can be obtained. In an example herein, the testes tissue can be obtained from at least one of humans, rats, mice, monkey, dogs, and any other organism. It is to be noted that the number of stages can vary with the organism. The obtained testes tissue specimen can be mounted over glass slides. Thereafter, the obtained and mounted testes tissue specimen can be dehydrated and embedded in a suitable material. In an embodiment herein, the dehydrated tissue can be embedded in melted paraffin wax. The embedded dehydrated tissue is then cut into thin tissue slices. In an embodiment herein, the dehydrated and embedded testes tissue can be mounted on a suitable mount and cut into thin tissue slices. In an example herein, a block from the dehydrated and embedded testes tissue is mounted on a microtome and cut into thin tissue slices. Thereafter, the tissue slices may be affixed to slides. After attaching the tissue slices to the slide, the material used for embedding the tissue is removed using a suitable means (such as a solvent). After removing the tissue from the material used for embedding, the tissue slices are rehydrated. In an embodiment, the rehydrated tissue slices can be stained. In an embodiment herein, the rehydrated tissue slices can be stained with at least one of Hematoxylin and Eosin (H&E) staining and Periodic acid-Schiff (PAS) staining. In an example, consider that H&E staining is used, wherein the Hematoxylin is mixed with a metallic salt or mordant, applied on the tissue slices, and counterstained with the Eosin. Excess stain is removed from the stained tissue slices using a weak acid solution.

For the assessment of the spermatogenesis using the obtained tissue slices, the processor 102 obtains a media (such as an image, video, and so on) of the slide with the stained tissue slices/sections. In an embodiment, the processor 102 obtains the media of the stained tissue slices/sections using the image sensors, cameras, and so on present in the electronic device 100. In an embodiment, the processor 102 obtains the media of the stained tissue slices/sections using the externally connected at least one of the image sensors, cameras, digital whole side image scanners, and so on.

The processor 102 can analyze the media for the assessment of spermatogenesis through a staging of seminiferous tubules. In an embodiment, the processor 102 may use at least one method/technique/model such as, Artificial Intelligence (AI) models, deep learning models, and so on for analyzing the stained tissue slices/sections (from the media). Embodiments herein further explained considering a deep learning model for the assessment of the spermatogenesis, but it should be obvious to a person skilled in the art that any other neural network/machine learning model can be considered.

Figure 1B:
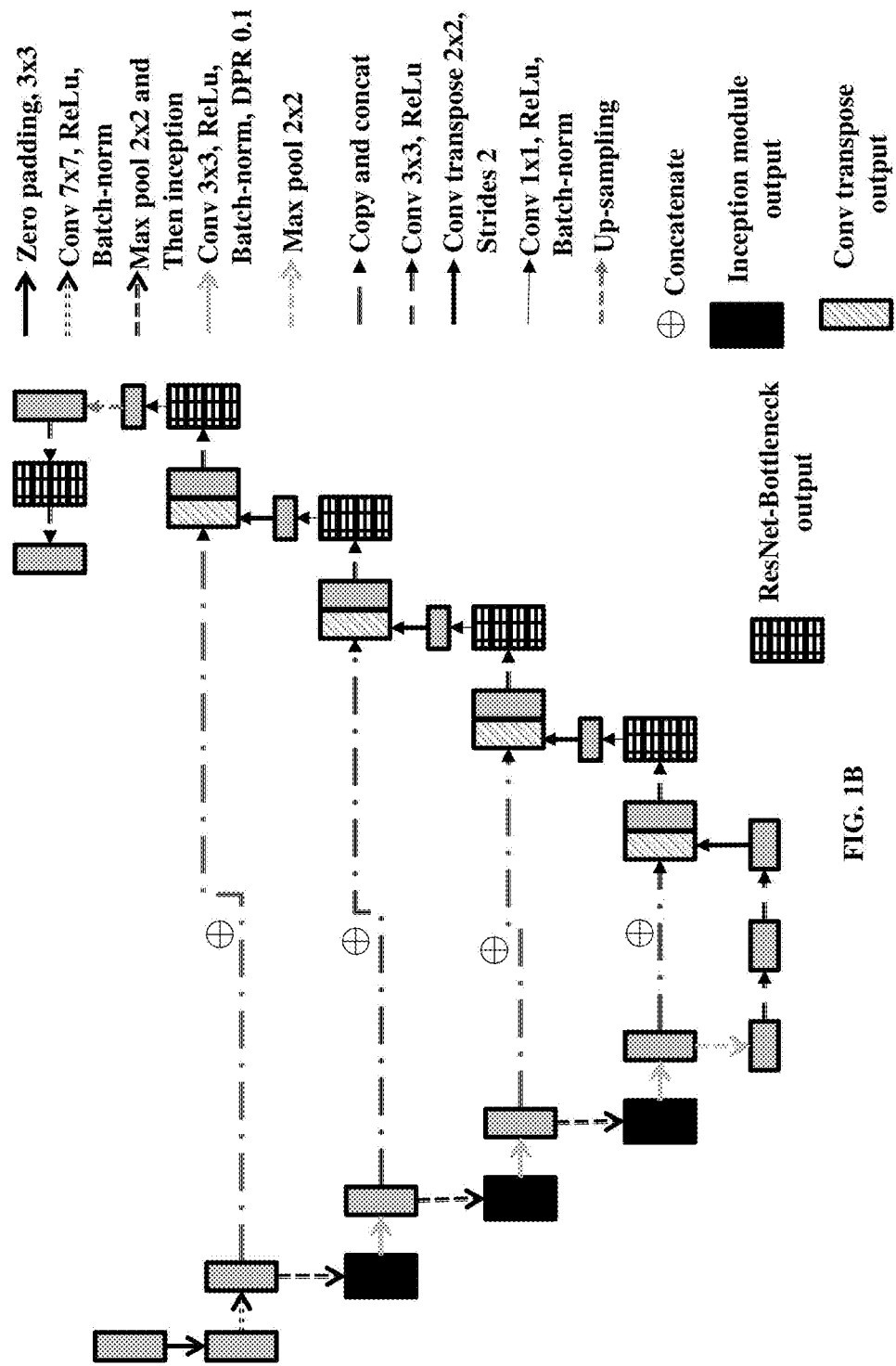
FIGS. 1B, 1C and 1D depict an example deep learning model used for an automated assessment of the spermatogenesis, according to embodiments as disclosed herein.
Figure 1C:
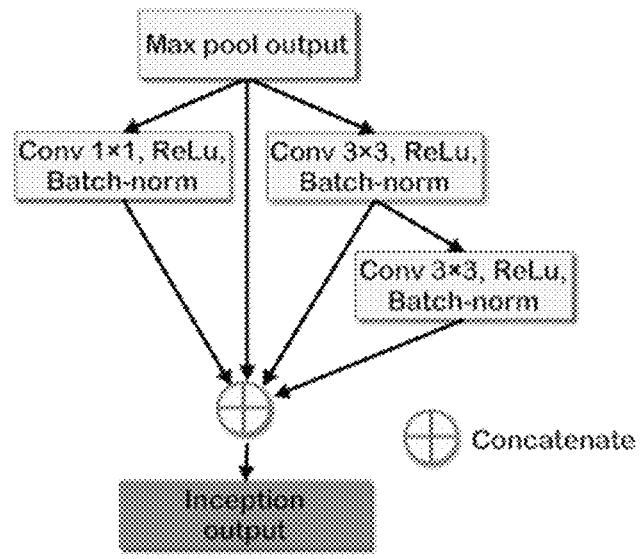

In an embodiment, the deep learning model can be a model capable of achieving one or more of detection, segmentation, and classification of objects (in an example herein, the objects can be the seminiferous tubules). Further, the deep learning model can achieve semantic segmentation of different classes in an input media. An example deep learning model used for the assessment of the spermatogenesis is illustrated in FIG. 1B. In an embodiment, the deep learning model includes an encoder subsystem/layer, and a decoder subsystem/layer that make an inference based on extracted features. The encoder subsystem includes three layers of an inception module. An example inception module is illustrated in FIG. 1C. The encoder subsystem comprises of an initial layer of zero padding followed by a convolution layer. Zero-padding layer increases the original media size by padding parameters. For example, a padding parameter of size 2 increases the width and height of input media by 4. The convolution layer is a matrix multiplication followed by additions. In this layer, a filter matrix is multiplied with the input media, wherein the size of the filter matrix is less than or equal to the input media size. An output of the convolution layer can be a media, which is half the size of the input media. The output of the convolution layer can be fed into a max pooling block/layer for down sampling. The max pooling layer takes the window-wise maximum pixel value from the input media. For example, a window of size 2×2 replaces the 2×2 submatrices from input media by the maximum pixel value from those 2×2 submatrices' pixels. Hence, the size of output media will be half of the input media size. The max pooling layer can be followed by the inception module (illustrated in FIG. 1C) with a short skip connection. The inception module may be followed by a successive convolution layer and a dropout layer. The dropout layer randomly nullifies the media pixel values based on user defined dropout rate. Further, a process of the max pooling layer and the inception module, and the convolution and the dropout layers can be repeated to derive an output from the encoder subsystem. In an example herein, the process of the max pooling layer and the inception module, and the convolution and the dropout layers can be repeated three times.

Figure 1D:
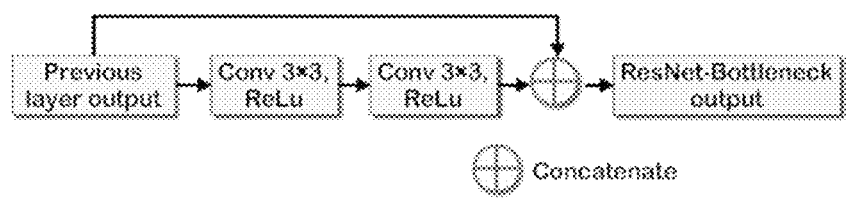

The decoder subsystem includes a deconvolution layer, wherein an output of the deconvolution layer is concatenated with the output of the encoder subsystem at a similar resolution. The deconvolution layer upsamples/increases the size of the media input using a suitable method such as, but not limited to, nearest neighbour method, convolution transpose method, and so on. The deconvolution layer upsamples the size of input media by the upsampling factor. The concatenation output may be followed by a ResNet-Bottleneck module. An example ResNet-Bottleneck module is illustrated in FIG. 1d. The ResNet-Bottleneck module includes two convolution layers, where a residue of an input of each convolution layer (which may be a short skip connection) may be added to an output of the convolution layers. This ensures properties of the encoder subsystem is available for later layers, so that outputs of the encoder and the decoder subsystems may not deviate from the original input. An output of the ResNet-Bottleneck module can be followed by a 1×1 convolution block to reduce the feature dimension and minimize over fitting issues. A process of the 1×1 convolution block can be repeated for a plurality of layers in the decoder subsystem with the last output layer in the decoder subsystem not having the 1×1 convolution block. In an example, a process of the 1×1 convolution block can be repeated for five layers in the decoder subsystem with the last output layer in the decoder subsystem not having the 1×1 convolution block.

The processor 102 analyzes the media of the stained tissue slices/sections using the deep learning model to detect the seminiferous tubules. By training a U-Net based deep learning model using a plurality of labels training data of a large number of images where one label is given to the region inside the tubules, another label is given to the periphery of the tubules and another label is given to the region outside the tubules. This data is further divided into training and validation datasets, where training data is used for training the deep learning model and validation dataset is used to validate the learned deep learning model. In an example herein, by training a U-Net based deep learning model using three labels training data of 1500 images where one label is given to the region inside the tubules, another label is given to the periphery of the tubules and the third label is given to the region outside the tubules. This data is further divided into training and validation datasets were training data is used for training the deep learning model and validation dataset is used to validate the learned deep learning model. In an example herein, the processor 102 uses the deep learning model that is trained on 512×512 tiles at 10× magnification.

The processor 102 maps the detected seminiferous tubules for accurate detection and segmentation of germ cells by mapping to a higher magnification. In an example herein, the processor 102 maps the detected seminiferous tubules from 10× to 40× magnification for the accurate segmentation of the germ cells. One tile at 10× resolution corresponds to 4 tiles at 40× resolution representing the same pixel information that is present at 10× resolution. This way, the tiles present at 10× resolution corresponding to that particular tubule are determined. Then the corresponding tiles are extracted at 40× resolution. Examples of the germ cells, can be but not limited to, elongated spermatids, spermatocytes, round spermatids, residual bodies, meiotic bodies, spermatogonia, or any other relevant markers. In an embodiment, the processor 102 uses at least one of a binary class segmentation model, a multi-class (semantic) segmentation model, and so on of the deep learning model to detect the germ cells. In an example herein, the binary class deep learning based model is used to segment out the elongated spermatids and sa six-class deep learning based model is used to segment out round spermatids of stage 1-9 and 14, round spermatids of stage 10, spermatogonia, meiotic bodies and pachytene. The processor 102 also displays an enhanced visualization of the segmented germ cells and other relevant features overlaid on the individual seminiferous tubules.

Once the germ cells are segmented, the processor 102 uses the segmented germ cells for performing a staging to classify the detected seminiferous tubules into respective stages of the spermatogenic cycle/spermatogenesis process. The germ cells present in individual tubules are first identified. Then corresponding to each tubule, a feature vector of 28 dimensions is formed by extracting features based on the size, position and number of various germ cells present therein. In an embodiment, the processor 102 uses a random forest classifier of the deep learning model to classify the detected seminiferous tubules into at least one stage. In accordance with the random forest classifier, the processor 102 uses characteristic features/stage attributes associated with each stage to classify the detected seminiferous tubules into respective stages of the spermatogenic cycle. Examples of the staging attributes can be, but not limited to, elongated spermatid heads bundling/location, spermatocytes, residual bodies, and so on. In an example herein, the detected seminiferous tubules can be classified into at least one of fourteen stages based on the characteristic feature/stage attributes associated with each stage and the detected staging attributes of the detected seminiferous tubules.

The processor 102 further classifies the detected seminiferous tubules into a normal category and an abnormal category based on the stages and morphological parameters. Examples of the parameters of the tubules present in the abnormal category are degenerated tubules, giant cell, Sertoli cell vacuolation, and so on. Embodiments herein can apply any machine learning based multiclass model to identify the stages. In an embodiment herein, based on the classification of the seminiferous tubules, the processor 102 generates a stage frequency table, wherein the table compares the seminiferous tubules of the normal category with the seminiferous tubules of the abnormal category. In an embodiment herein, the processor 102 can fetch a pre-generated stage frequency table. The stage frequency table lists the stage frequencies corresponding to individual stage numbers. The stage frequencies are calculated by dividing the number of tubules in that particular stage by the total number of tubules analyzed in the testes.

The processor 102 can be also configured to classify the obtained testes tissue specimen into the normal category and the abnormal category based on the classification of the seminiferous tubules into the normal and abnormal categories and the generated stage frequency table. This classification is of importance in preclinical drug toxicology testing, where toxicity associated with a new drug is tested on animal tissue. If there are abnormalities occurring in animals after dosage, then the drug can be considered to be a failure.

The processor 102 can be further configured to classify a molecule or chemical present in the obtained testes tissue specimen into the normal and the abnormal based on the classification of the testes tissue specimen. The processor 102 further generates reports based on quantified parameters. The report includes information such as, but not limited to, detailed analysis of each of the tubules, frequency map of fourteen stages, abnormalities, visualization(s) of the stages overlaid on individual tubules, and so on.

The memory 104 stores at least one of the obtained media of the stained tissue slices, the stage frequency table, the classifications, and so on. The memory 104 may also store program code/instructions that can be executed on the processor 102 to perform the automated assessment of the spermatogenesis. Further, the memory 104 may include one or more computer-readable storage media. The memory 104 may include non-volatile storage elements. Examples of such non-volatile storage elements may include magnetic hard discs, optical discs, floppy discs, flash memories, or forms of electrically programmable memories (EPROM) or electrically erasable and programmable (EEPROM) memories. In addition, the memory 104 may, in some examples, be considered a non-transitory storage medium. The term "non-transitory" may indicate that the storage medium is not embodied in a carrier wave or a propagated signal. However, the term "non-transitory" should not be interpreted to mean that the memory 104 is non-movable. In some examples, the memory 104 can be configured to store larger amounts of information than the memory. In certain examples, a non-transitory storage medium may store data that can, over time, change (e.g., in Random Access Memory (RAM) or cache).

The communication interface 106 can be configured to enable the electronic device 100 to connect with the at least one external entity (such as, the server, the external database, the user devices, the imaging sensors/scanners, and so on) using the communication network.

The I/O module 108 can be configured to enable the electronic device 100 to connect with at least one of the imaging sensors, scanners, cameras, and so on to capture the media of the stained tissue slices.

The display 110 can be configured to display the enhanced visualization of the detected seminiferous tubules and the associated into stages and so on.

FIG. 1 shows exemplary blocks of the electronic device 100, but it is to be understood that other embodiments are not limited thereon. In other embodiments, the electronic device 100 may include less or more number of blocks. Further, the labels or names of the blocks are used only for illustrative purpose and does not limit the scope of the embodiments herein. One or more blocks can be combined together to perform same or substantially similar function in the electronic device 100.

Figure 2A:
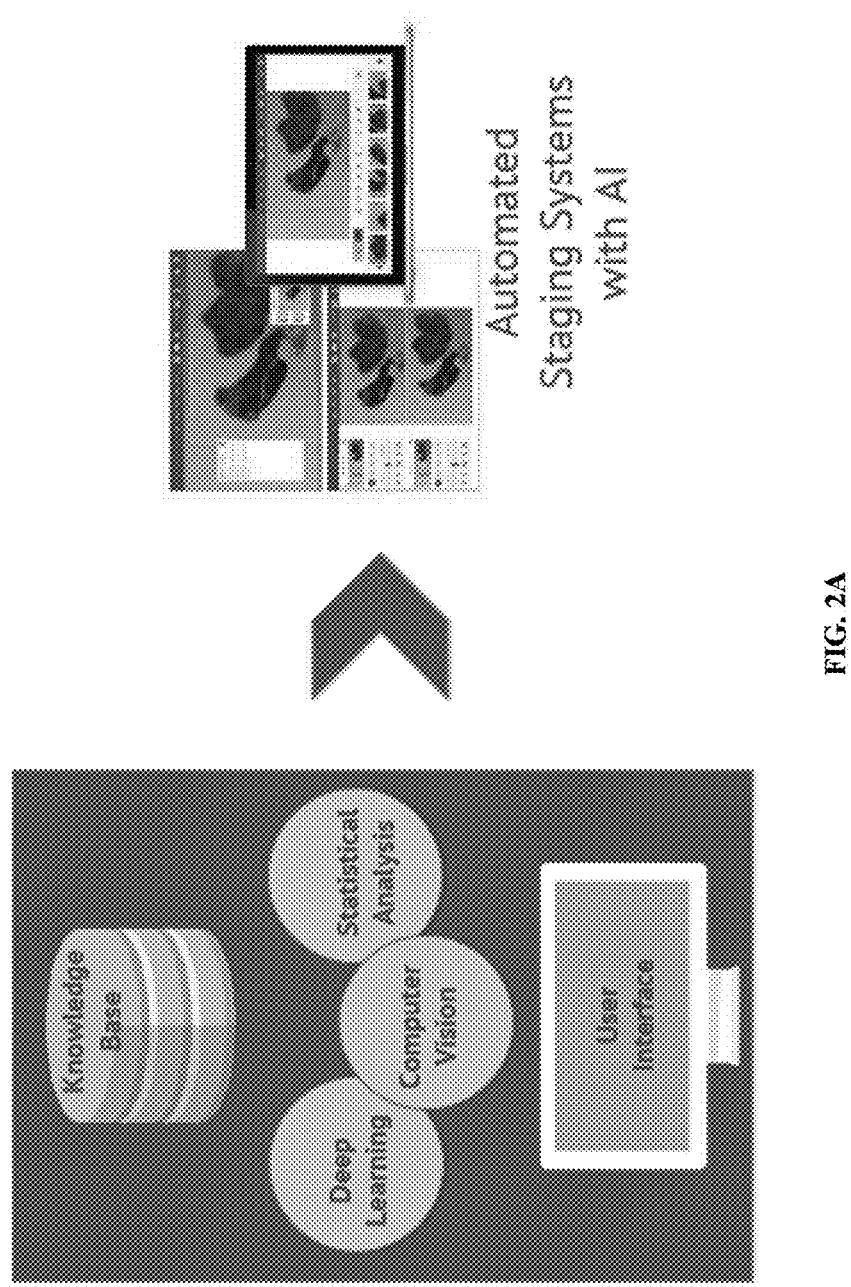
FIG. 2A is an example diagram depicting the automated assessment of the spermatogenesis, according to embodiments as disclosed herein.

FIG. 2A is an example diagram depicting automated assessment of the spermatogenesis, according to embodiments as disclosed herein. Embodiments herein enable the electronic device 100 to perform the automated assessment of the spermatogenesis for toxicology analysis on the male reproductive function. As illustrated in FIG. 2A, the electronic device 100 may use at least one of the AI model, the deep learning model, Computer Vision (CV) techniques, and so on to perform the automated assessment of the spermatogenesis. The electronic device 100 may further display the enhanced visualization of the spermatogenesis using a User Interface (UI)/display 110.

Figure 2B:
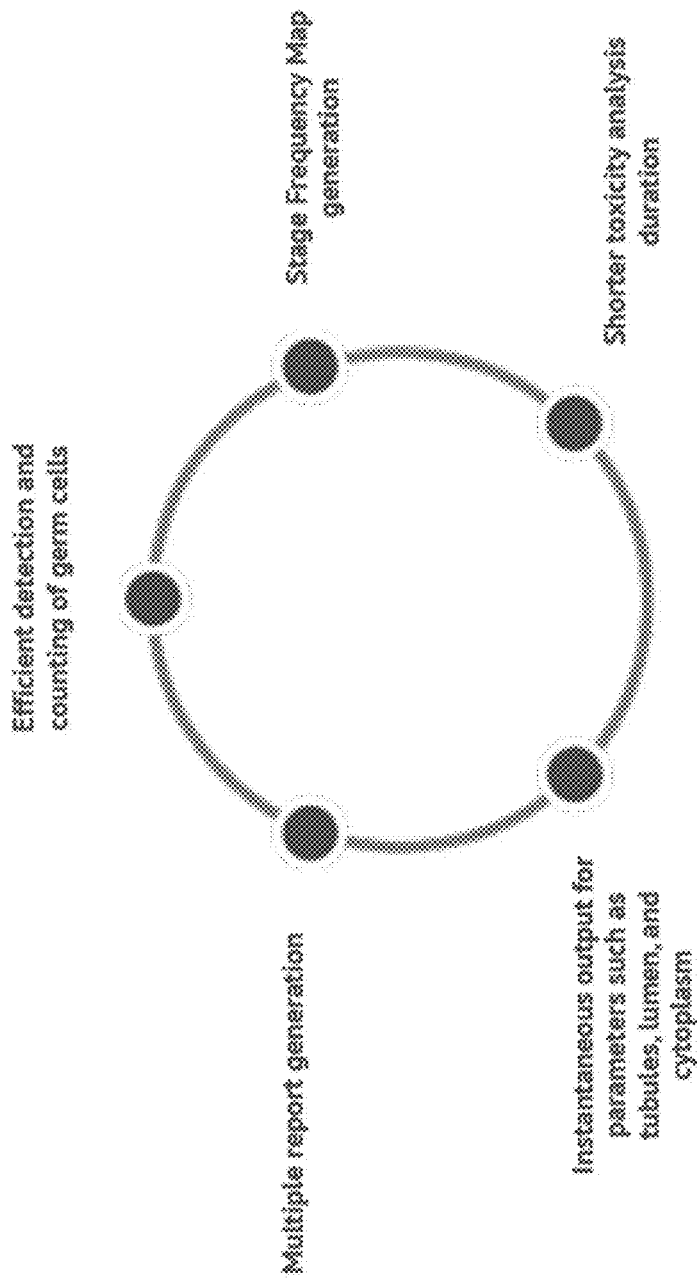
FIG. 2B is an example diagram depicting benefits of the automated assessment of the spermatogenesis, according to embodiments as disclosed herein.

As illustrated in FIG. 2B, the automated assessment of the spermatogenesis may result in providing instantaneous output for parameters such as tubules, lumen, cytoplasm, and so on, generation of multiple reports providing information related to the assessment of the spermatogenesis cytoplasm, efficient detection and counting of the germ cells, generation of the stage frequency table, shorter toxicity analysis duration, and so on.

Figure 3:
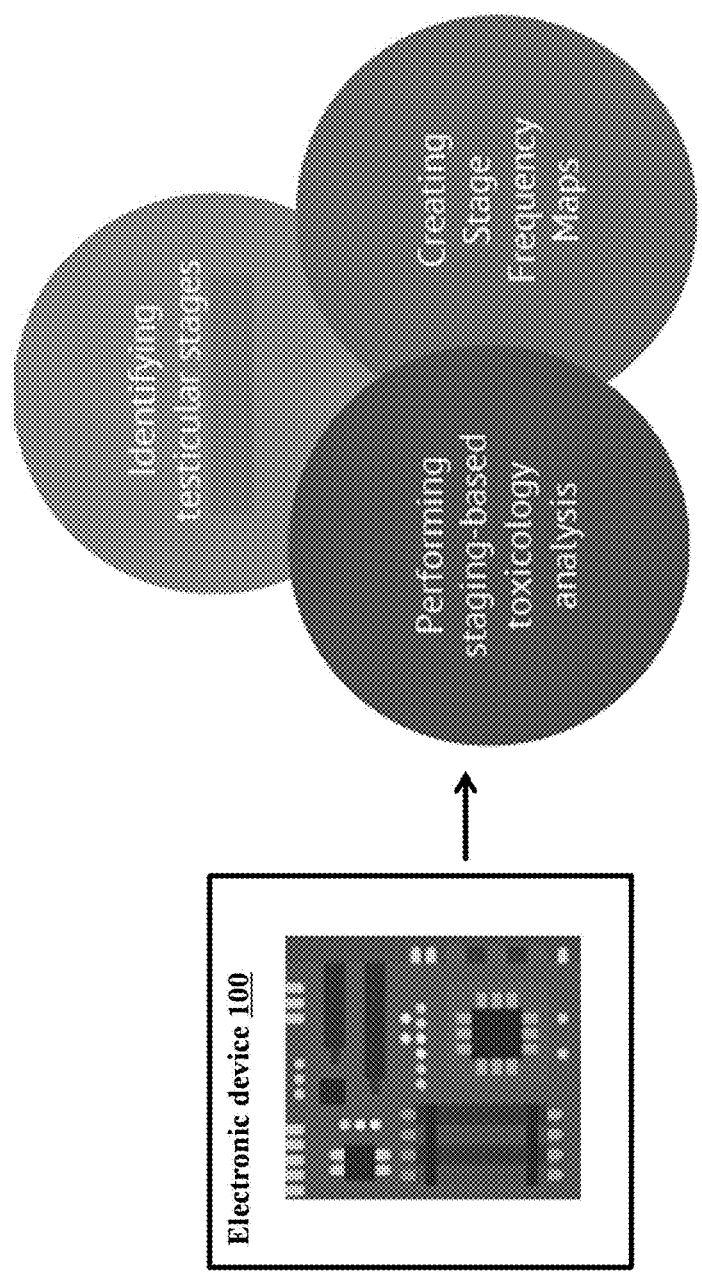
FIG. 3 depicts an example electronic device for the automated assessment of the spermatogenesis, according to embodiments as disclosed herein.
Figure 4:
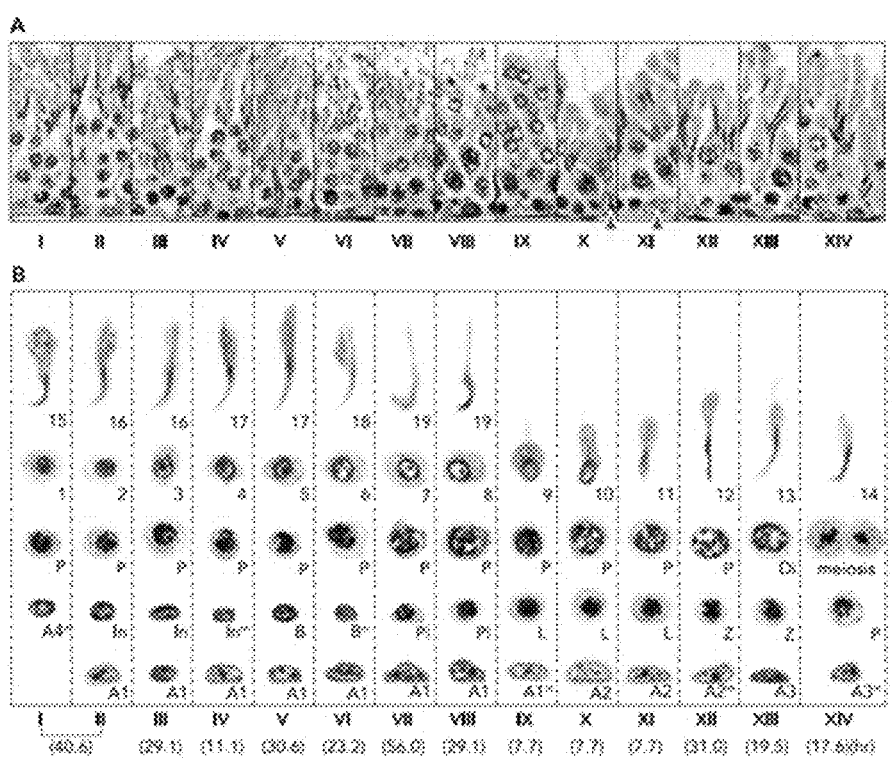
FIG. 4 is an example diagram depicting seminiferous tubules, according to embodiments as disclosed herein.
Figure 5A:
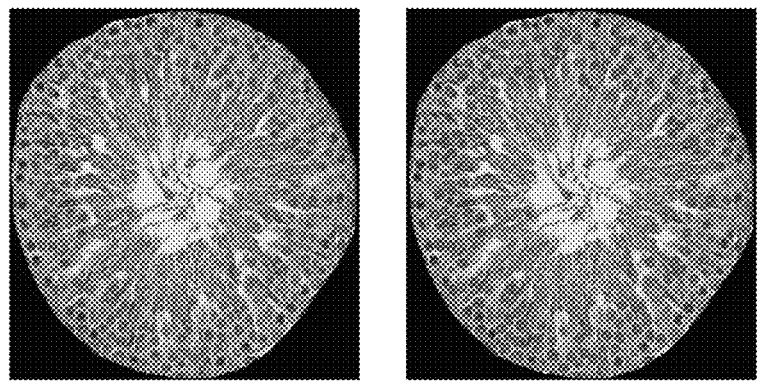
FIGS. 5A, 5B, 5C, 5D and 5E are example diagrams depicting segmentation of germ cells, according to embodiments as disclosed herein.
Figure 5B:
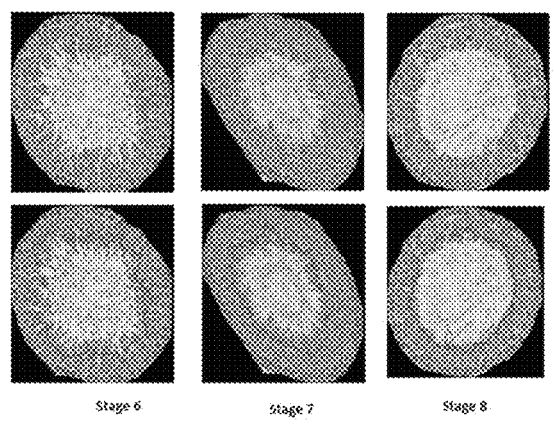
Figure 5C:
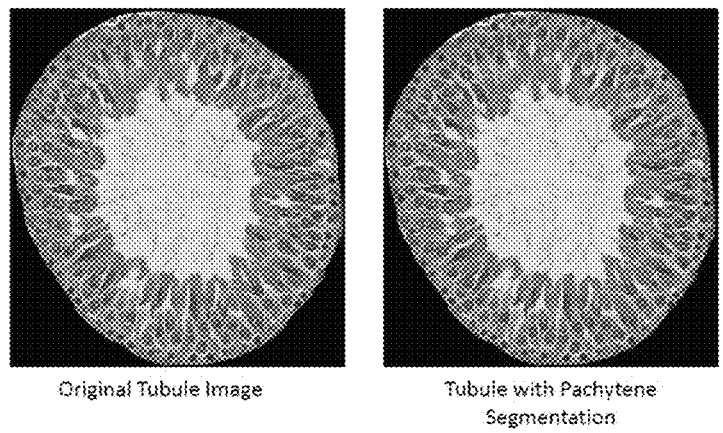
Figure 5D:
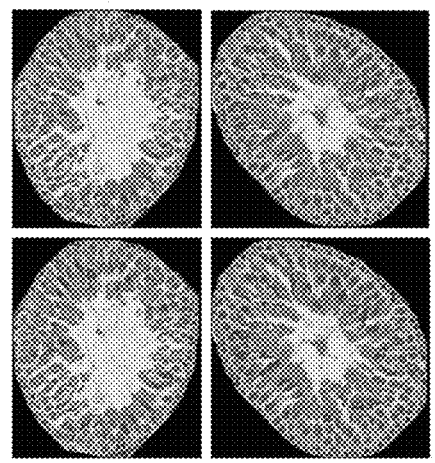
Figure 5E:
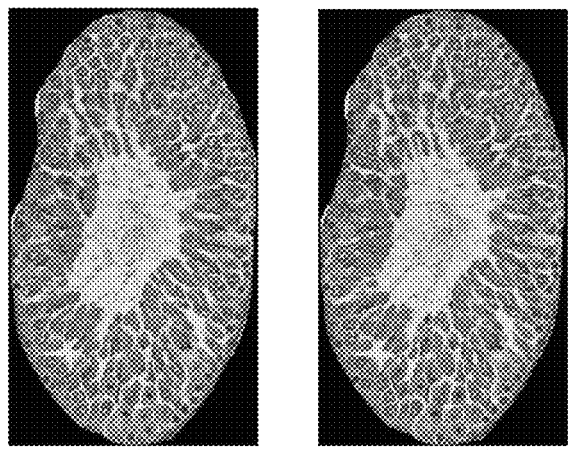

FIG. 3 depicts an example electronic device 100 for the automated assessment of the spermatogenesis, according to embodiments as disclosed herein. Embodiments herein enable the electronic device 100 to perform the automated assessment of the spermatogenesis through the seminiferous tubules. The electronic device 100 obtains the testes tissue specimen. The electronic device 100 uses at least one of the deep learning model, the AI model, and so on to analyze the obtained testes tissue specimen and detects the seminiferous tubules. Example seminiferous tubules are illustrated in FIG. 4.

The electronic device 100 maps the detected seminiferous tubules and segments the germ cells. The segmented germ cells can be at least one of elongated spermatids, spermatocytes, round spermatids, residual bodies, meiotic bodies, spermatogonia, basophilic granules/residual bodies, pachytene or any other relevant markers. In an example herein, a round spermatids segmentation, a basophilic granules/residual bodies with lumen area segmentation, a pachytene segmentation, an elongated spermatids segmentation, a meiotic bodies segmentation is illustrated in FIGS. 5A-5E.

Figure 6A:
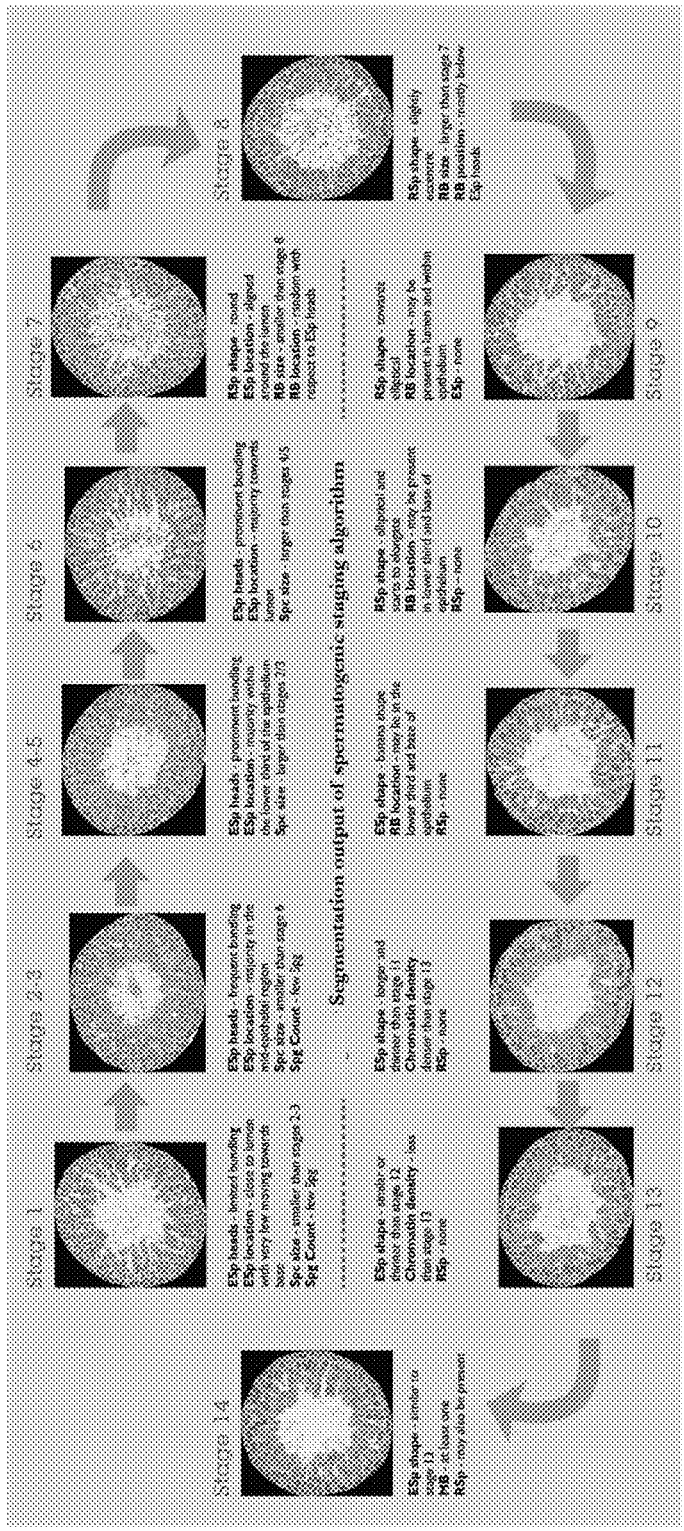
Figure 6C:
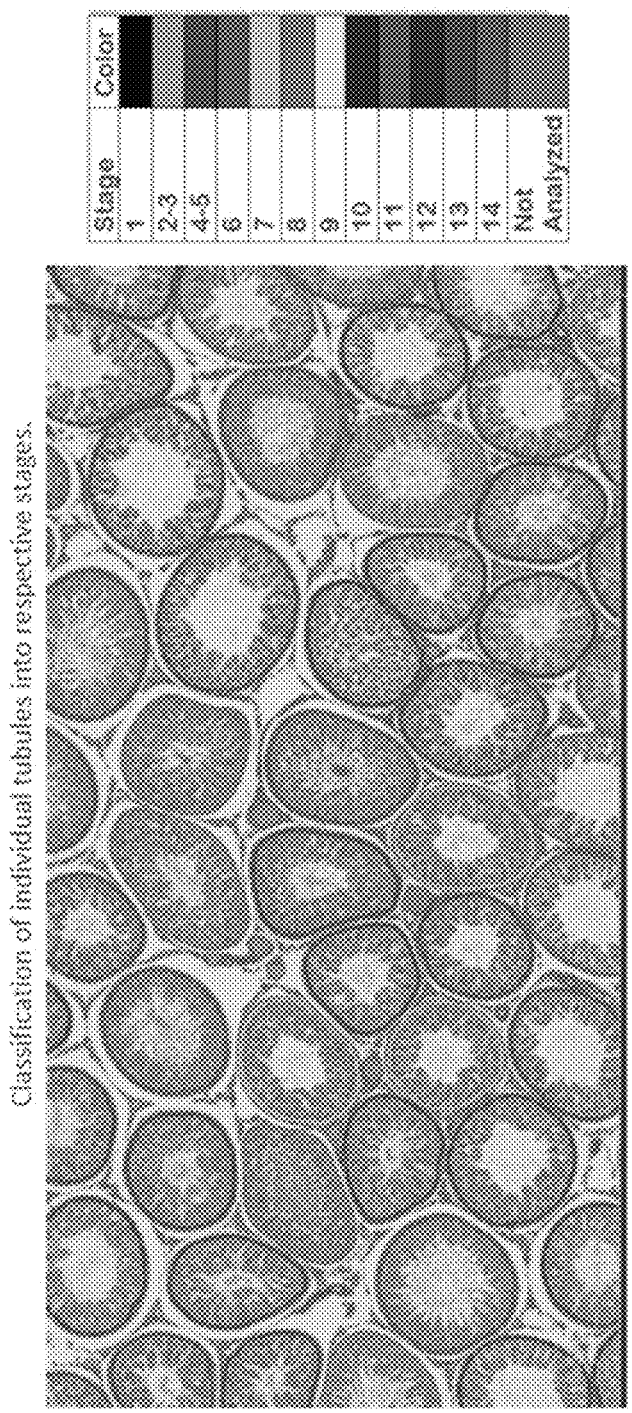

Based on the segmented germ cells, the electronic device 100 classifies the individual seminiferous tubules into the respective stages of the spermatogenic cycle based on the segmented germ cells. The electronic device 100 can classify the individual seminiferous tubules into the respective stages based on the random forest classifier as illustrated in FIG. 6A. In accordance with the random forest classifier, the electronic device 100 uses the characteristic features and staging attributes. Examples of the staging attributes can be, but not limited to, elongated spermatid heads bundling/location, spermatocytes, residual bodies, and so on. In an example herein, the characteristics features/staging attributes associated with each stage are illustrated in FIG. 6B. In an example herein, the electronic device 100 classifies the individual seminiferous tubules into the fourteen stages as illustrated in FIG. 6C.

Figure 6D:
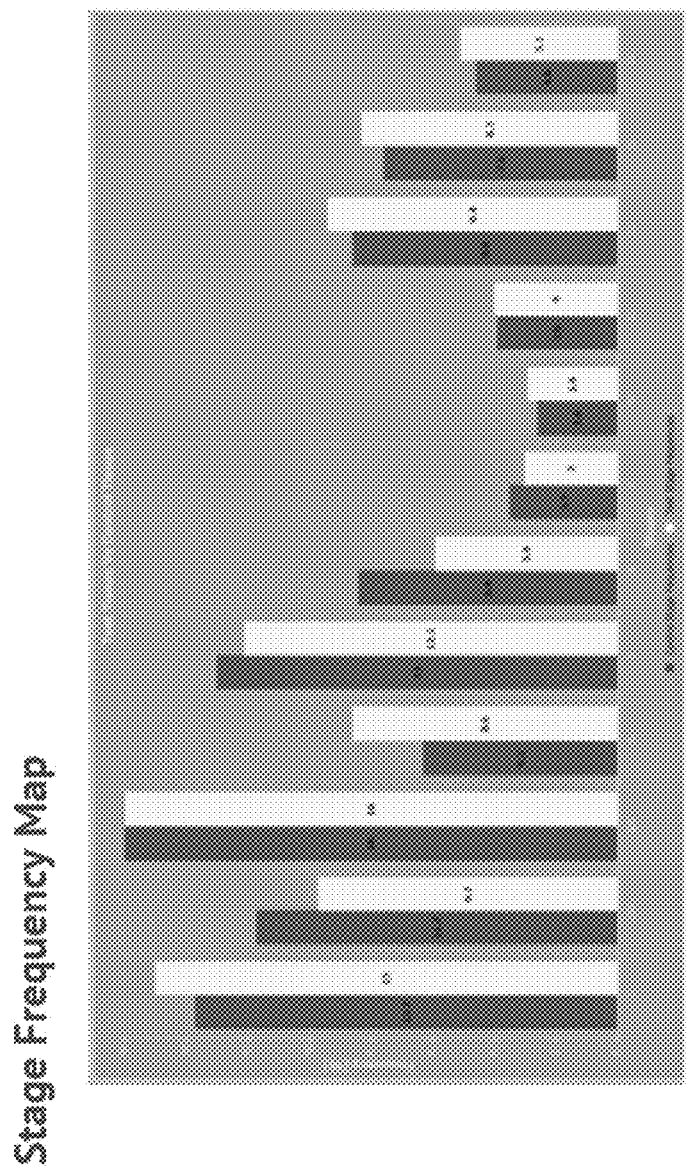

The electronic device 100 further classifies the seminiferous tubules into the normal category and the abnormal category based on the classification of the individual seminiferous tubules into the respective stages and the segmented germ cells. The electronic device 100 further generates the stage frequency table for comparing the seminiferous tubules of the normal category with the seminiferous tubules of the abnormal category. In an example herein, the stage frequency table/map is illustrated in FIG. 6D.

Figure 6E:
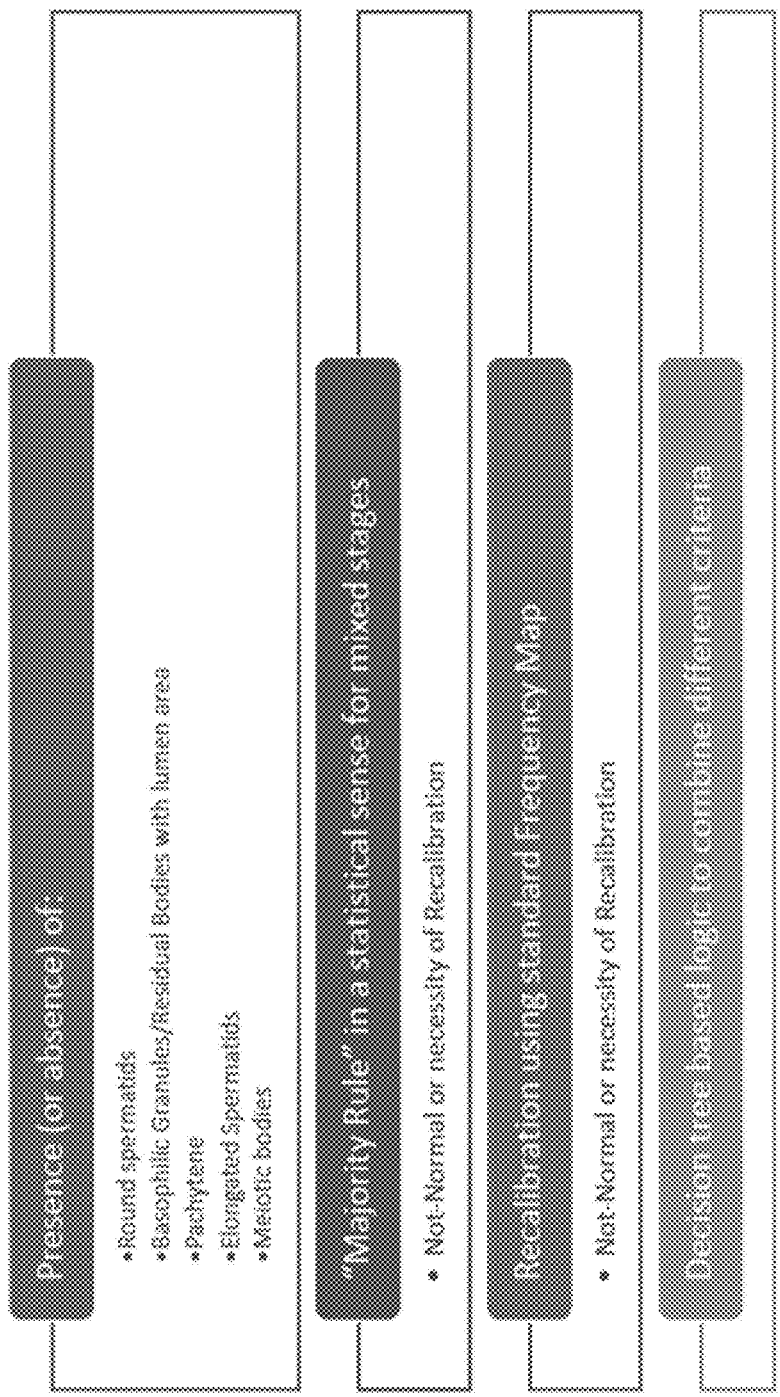

Once the seminiferous tubules are classified into the normal category and the abnormal category, the electronic device 100 classifies the obtained testes tissue specimen into the normal category and the abnormal category using staging criteria. Examples of the staging criteria can be, but not limited to, presence or absence of the segmentation of the germ cells (the round spermatids segmentation, the basophilic granules/residual bodies with lumen area segmentation, the pachytene segmentation, an elongated spermatids segmentation, the meiotic bodies segmentation, or the like), a majority rule in a statistical sense for mixed stages (abnormal or necessity of recalibration), recalibration using the stage/standard frequency table/map, a decision tree based logic to combine different criteria, and so on. In an example herein, the staging criteria are illustrated in FIG. 6E.

Figure 6F:
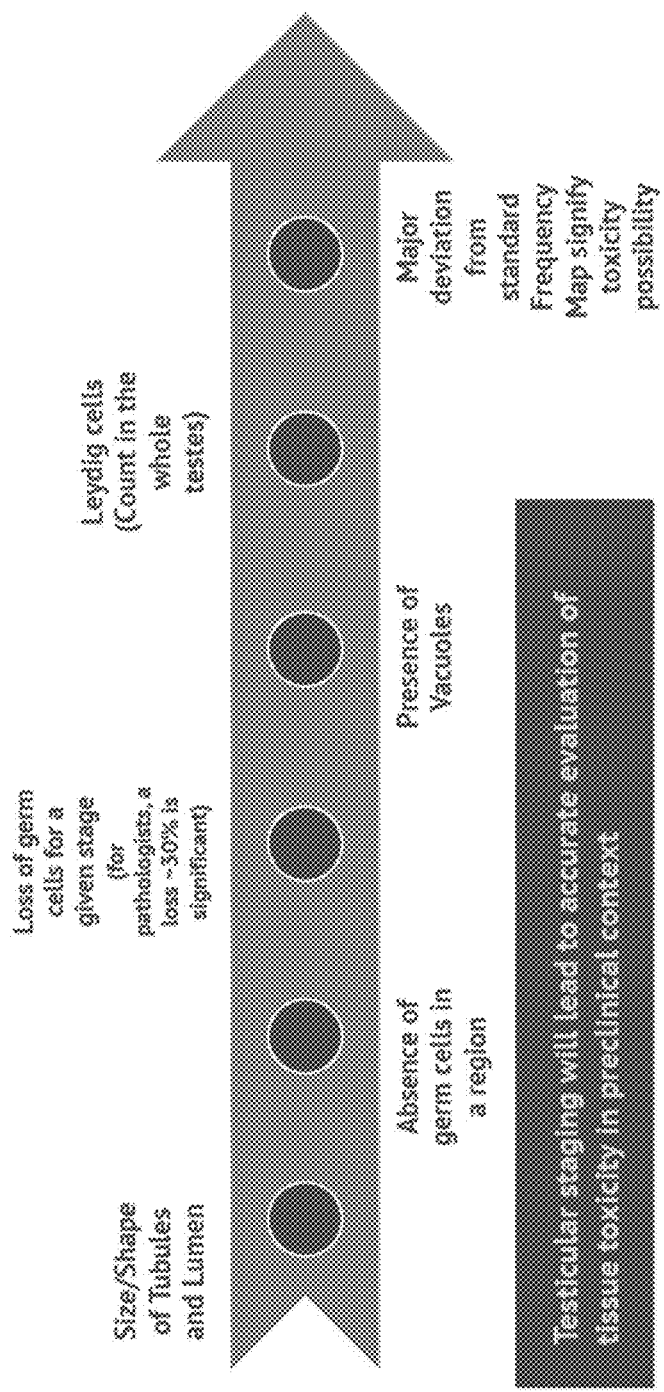

As illustrated in FIG. 6F, the staging of the testes tissue specimen may lead to accurate evaluation of the tissue toxicity in preclinical context. The electronic device 100 identifies size/shape of the seminiferous tubules/lumen while performing the staging. Further, the electronic device 100 detects presence or absence of the germ cells for a given region, and loss of the germ cells for a given stage. Thereafter, the electronic device 100 detects presence of vacuoles, and a count of Leydig cells in the obtained whole testes. Based on the count of the cells, the electronic device 100 can determine a major deviation from the standard frequency map, wherein the major deviation from the standard frequency map indicates toxicity possibility.

Figure 7:
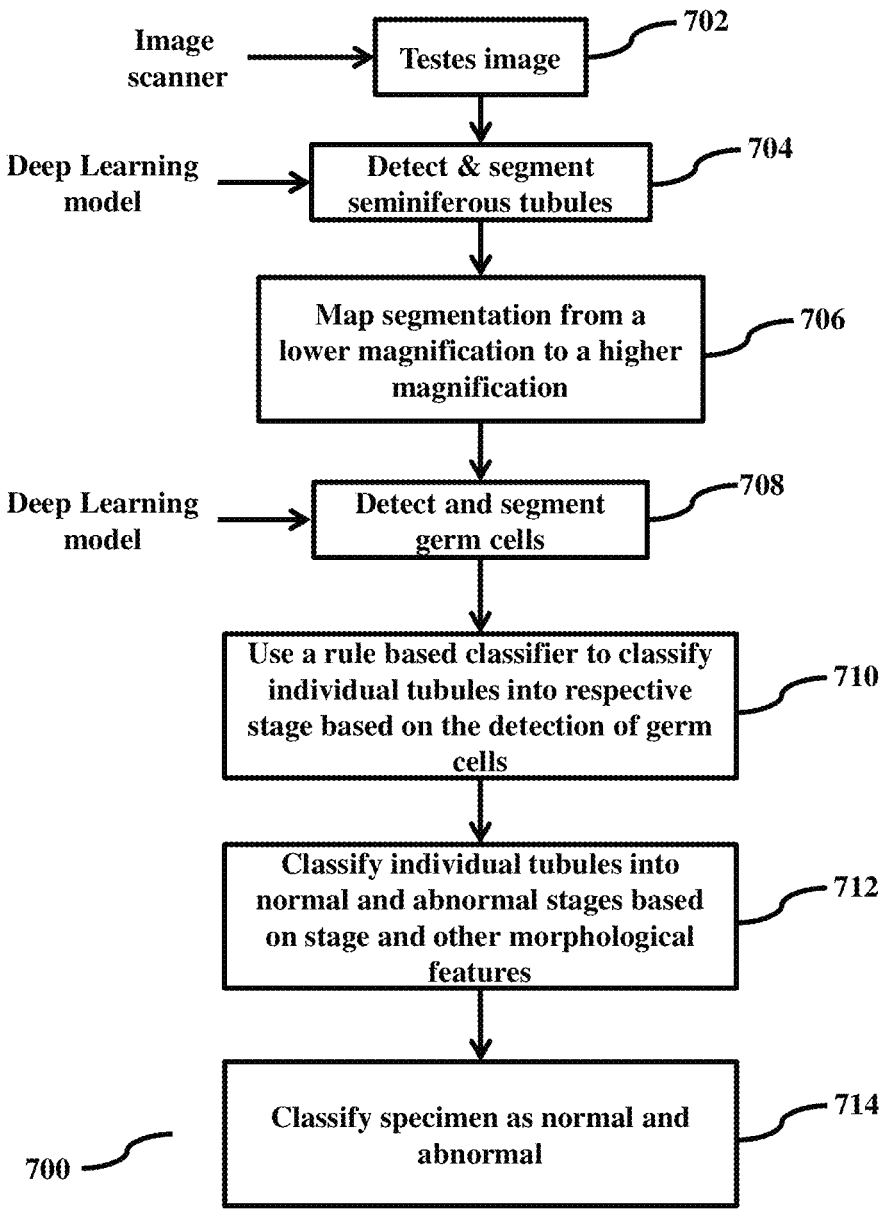
FIG. 7 is an example diagram depicting a method for automated assessment of the spermatogenesis, according to embodiments as disclosed herein.

FIG. 7 is an example diagram depicting a method for automated assessment of the spermatogenesis, according to embodiments as disclosed herein. The electronic device 100 obtains (at step 702) the media of the stained tissue slices. The electronic device 100 detects and segments (at step 704) the seminiferous tubules by analyzing the media of the stained tissue slices. The electronic device 100 (at step 706) maps the segmentation of the seminiferous tubules from a lower magnification to a higher magnification. The electronic device 100 detects and segments (at step 708) the germ cells from the segmented seminiferous tubules. The germ cells can be segmented into at least one of the round spermatid segmentation, the basophilic granules/residual bodies with lumen area segmentation, the pachytene segmentation, the elongated spermatids segmentation, the meiotic bodies segmentation, or the like. The electronic device 100 classifies (at step 710) the seminiferous tubules uses the random forest classifier based on the segmented germ cells into the respective stages. The electronic device 100 further categorizes (at step 712) the seminiferous tubules into the normal category and the abnormal category based on the classification of the seminiferous tubules into the respective stages and the morphological features/parameters. The electronic device 100 classifies (at step 714) the obtained testes tissue specimen into the normal category and the abnormal category for detecting toxological effects on the male reproductive function. The various actions in method 700 may be performed in the order presented, in a different order or simultaneously. Further, in some embodiments, some actions listed in FIG. 7 may be omitted.

Figure 8:
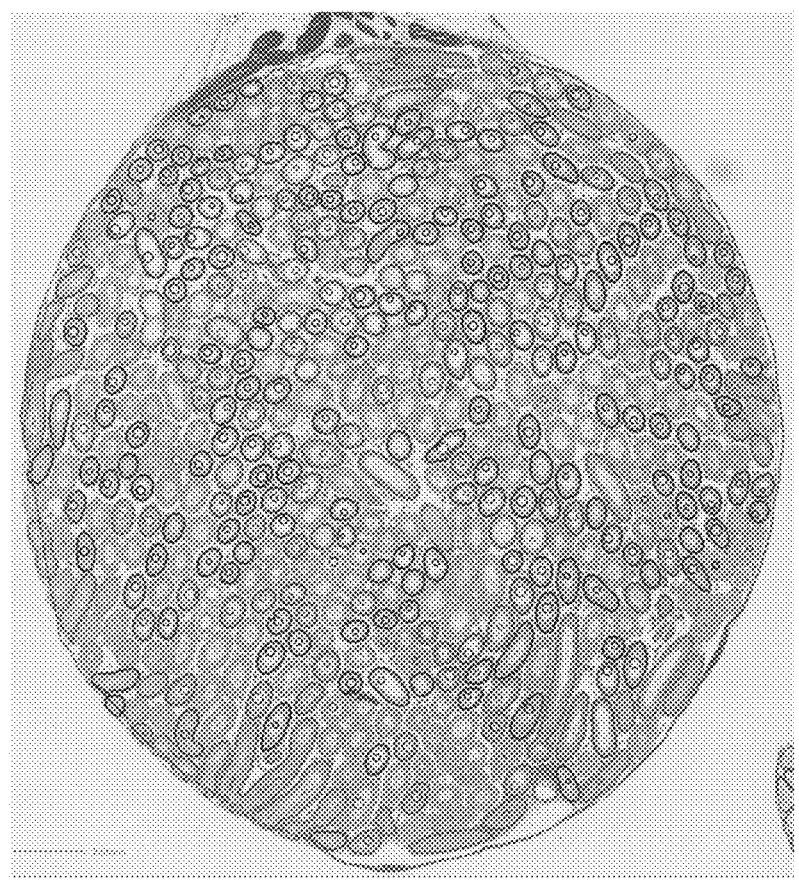
FIG. 8 is an example diagram depicting a result of the automated spermatogenic staging, according to embodiments as disclosed herein.

FIG. 8 is an example diagram depicting a result of the automated spermatogenic staging, according to embodiments as disclosed herein.

Figure 9:
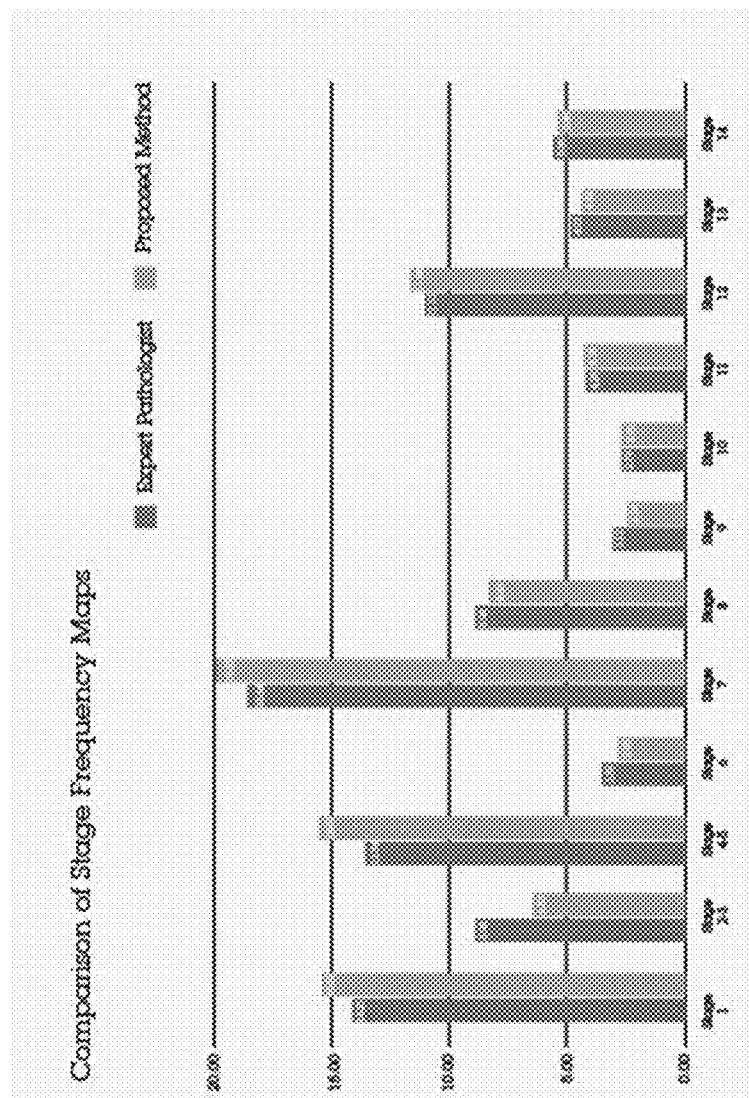
FIG. 9 is an example graph depicting a comparison of the stage frequency map generated based on the automated staging and a stage frequency map generated by an expert pathologist, according to embodiments as disclosed herein.

FIG. 9 is an example graph depicting a comparison of the stage frequency map generated based on the automated staging and a stage frequency map generated by an expert pathologist, according to embodiments as disclosed herein.

FIG. 10 is an example table depicting average accuracy and average precision resulted from the automated spermatogenic staging, according to embodiments as disclosed herein.

Embodiments herein provide an analytical aid to assess spermatogenesis through a staging of seminiferous tubules.

Embodiments herein provide an accurate, reproducible, faster assessment of the spermatogenesis through an automated staging of seminiferous tubules, which eliminates a need for an expertise pathologist.

Embodiments herein facilitate the automated assessment of the spermatogenesis without requiring extra stained tissue slices/sections such as a Periodic Acid Schiff (PAS) stained tissue slices, or the like.

Embodiments herein detect and classify the seminiferous tubules into different stages/classes automatically using a deep learning/Artificial Intelligence method.

Embodiments herein provide an enhanced visualization of the detected seminiferous tubules and the associated stages.

Embodiments herein perform an automated assessment of stage aware abnormalities to classify the seminiferous tubules into a normal category and an abnormal category.

Embodiments herein perform an automated assessment of testes tissue specimen and molecules/chemicals to classify the testes tissue specimen and the molecules/chemicals into the normal category and the abnormal category.

The embodiments disclosed herein can be implemented through at least one software program running on at least one hardware device and performing network management functions to control the network elements. The network elements shown in FIG. 1 include blocks which can be at least one of a hardware device, or a combination of hardware device and software module.

The embodiment disclosed herein discloses method and systems for automated assessment of spermatogenesis. Therefore, it is understood that the scope of the protection is extended to such a program and in addition to a computer readable means having a message therein, such computer readable storage means contain program code means for implementation of one or more steps of the method, when the program runs on a server or mobile device or any suitable programmable device. The method is implemented in at least one embodiment through or together with a software program written in e.g. Very high speed integrated circuit Hardware Description Language (VHDL) another programming language, or implemented by one or more VHDL or several software modules being executed on at least one hardware device. The hardware device can be any kind of portable device that can be programmed. The device may also include means which could be e.g. hardware means like e.g. an ASIC, or a combination of hardware and software means, e.g. an ASIC and an FPGA, or at least one microprocessor and at least one memory with software modules located therein. The method embodiments described herein could be implemented partly in hardware and partly in software. Alternatively, the invention may be implemented on different hardware devices, e.g. using a plurality of CPUs.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of embodiments, those skilled in the art will recognize that the embodiments herein can be practiced with modification within the spirit and scope of the embodiments as described herein.

We claim:

1. A method for performing automated assessment of spermatogenesis of a testes tissue specimen, the method comprising
analyzing, by an electronic device (100), a media of a mounted slice of a stained testes tissue specimen to detect at least one seminiferous tubule;
performing, by the electronic device (100), segmentation of at least one germ cell in the media of the mounted slice of the stained testes tissue specimen by mapping the detected at least one seminiferous tubule to a higher magnification level;
classifying, by the electronic device (100), the detected at least one seminiferous tubule into at least one stage of spermatogenic cycle/spermatogenesis process by performing a staging using the at least one segmented germ cell;
classifying, by the electronic device (200), the at least one detected seminiferous tubule into at least one of a normal category and an abnormal category based on the stage into which the detected at least one seminiferous tubule in classified and at least one morphological parameter associated with the testes tissue; and
classifying, by the electronic device (200), the testes tissue specimen into at least one of a normal category and an abnormal category based on classification of the at least one seminiferous tubules into at least one of a normal category and at least one abnormal category and a stage frequency table.

2. The method, as claimed in claim 1, wherein the method comprises
mounting the testes tissue specimen on a glass slide;
dehydrating the mounted testes tissue specimen;
embedding the dehydrated mounted testes tissue specimen in melted paraffin wax;
cutting the embedded dehydrated mounted testes tissue specimen into at least one slice;
removing the melted paraffin wax from the at least one slice of the embedded dehydrated mounted testes tissue specimen;
rehydrating the at least one slice of the dehydrated mounted testes tissue specimen; and
staining the at least one slice of the rehydrated mounted testes tissue specimen.

3. The method, as claimed in claim 2, wherein cutting the embedded dehydrated mounted testes tissue specimen comprises
mounting a block from the embedded dehydrated mounted testes tissue specimen on a microtome; and
cutting at least one tissue slice from the mounted block.

4. The method, as claimed in claim 2, wherein the at least one slice of the rehydrated mounted testes tissue specimen is stained with Hematoxylin and Eosin (H&E) staining, which comprising
mixing Hematoxylin with a metallic salt or mordant;
applying the mixed Hematoxylin on the tissue slices;
counterstaining the tissue slices with Eosin; and
removing excess stain from the stained tissue slices using a weak acid solution.

5. The method, as claimed in claim 1, wherein the at least one germ cell is detected using at least one of a binary class segmentation model, and a multi-class (semantic) segmentation model.

6. The method, as claimed in claim 1, wherein the germ cell is at least one of elongated spermatids, spermatocytes, round spermatids, residual bodies, meiotic bodies, and spermatogonia.

7. The method, as claimed in claim 1, wherein a random forest classifier classifies the detected at least one seminiferous tubule into at least one stage of spermatogenic cycle using at least one characteristic feature associated with each stage.

8. The method, as claimed in claim 1, wherein a molecule or a chemical present in the obtained testes tissue specimen is classified into at least one of a normal category and an abnormal category based on the classification of the testes tissue specimen.

9. The method, as claimed in claim 1, wherein the stage frequency table compares at least one seminiferous tubule of a normal category with at least one seminiferous tubule of an abnormal category.

10. An electronic device (100) configured for
analyzing a media of a mounted slice of a stained testes tissue specimen to detect at least one seminiferous tubule;
performing segmentation of at least one germ cell in the media of the mounted slice of the stained testes tissue specimen by mapping the detected at least one seminiferous tubule to a higher magnification level;

classifying the detected at least one seminiferous tubule into at least one stage of spermatogenic cycle/spermatogenesis process by performing a staging using the at least one segmented germ cell;

classifying the at least one detected seminiferous tubule into at least one of a normal category and an abnormal category based on the stage into which the detected at least one seminiferous tubule in classified and at least one morphological parameter associated with the testes tissue; and classifying the testes tissue specimen into at least one of a normal category and an abnormal category based on classification of the at least one seminiferous tubules into at least one of a normal category and at least one abnormal category and a stage frequency table.

11. The electronic device, as claimed in claim 10, wherein the electronic device is configured for dehydrating a mounted testes tissue specimen;

embedding the dehydrated mounted testes tissue specimen in melted paraffin wax;

cutting the embedded dehydrated mounted testes tissue specimen into at least one slice;

removing the melted paraffin wax from the at least one slice of the embedded dehydrated mounted testes tissue specimen;

rehydrating the at least one slice of the dehydrated mounted testes tissue specimen; and staining the at least one slice of the rehydrated mounted testes tissue specimen.

12. The electronic device, as claimed in claim 10, wherein the electronic device is configured for detecting the at least one germ cell using at least one of a binary class segmentation model, and a multi-class (semantic) segmentation model, wherein the germ cell is at least one of elongated spermatids, spermatocytes, round spermatids, residual bodies, meiotic bodies, and spermatogonia.

13. The electronic device, as claimed in claim 10, wherein the electronic device is configured for using a random forest classifier to classify the detected at least one seminiferous tubule into at least one stage of spermatogenic cycle using at least one characteristic feature associated with each stage.

14. The electronic device, as claimed in claim 10, wherein the electronic device is configured for classifying a molecule or a chemical present in the obtained testes tissue specimen into at least one of a normal category and an abnormal category based on the classification of the testes tissue specimen.

* * * * *